US00PP11377P

United States Patent [19]

Heims

[11] Patent Number: Plant 11,377

[45] Date of Patent: May 9, 2000

[54] HEUCHERA PLANT NAMED 'CHERRIES JUBILEE'

[75] Inventor: Dan M. Heims, Portland, Oreg.

[73] Assignee: Terra Nova Nurseries, Inc., Tigard, Oreg.

[21] Appl. No.: 09/108,341

[22] Filed: Jun. 30, 1998

[51] Int. Cl.[7] ..... A01H 5/00

[52] U.S. Cl. ..... Plt./263

[58] Field of Search ..... Plt./263

[56] References Cited

PUBLICATIONS

GTITM UPOVROM Citation for 'Cherries Jubilee' as per QZ PBR 980692.

*Primary Examiner*—Howard J. Locker
*Assistant Examiner*—Kent L. Bell
*Attorney, Agent, or Firm*—Klarquist Sparkman Campbell Leigh & Whinston, LLP

[57] ABSTRACT

A new and distinct hybrid of Heuchera plant characterized by cherry-red flowers and chocolate-toned foliage.

1 Drawing Sheet

The present invention relates to a new and distinct hybrid of Heuchera, which originated as a cross-pollination of a select unnamed red-flowered *Heuchera sanguinea* (female parent, unpatented) and Heuchera 'Whirlwind' (male parent, unpatented), a pink-flowered and bronze-leaved hybrid.

The new Heuchera is a result of a controlled cross of the aforementioned plants at Terra Nova Nurseries, Inc., in Canby, Oreg. This hybrid was selected from a large selection of seedlings. Seed and pollen parent plants were retained to observe habit and to compare with the instant plant. The new variety has been reproduced only by asexual propagation (division and tissue culture). Each of the progeny exhibits identical characteristics to the original plant and is unlike any Heuchera offered by any American nursery or book known to me as evidenced by the following characteristics:

(1) Summer, fall and winter: chocolate-toned foliage.

(2) Spring: cherry-red flowers.

Asexual propagation by division and tissue-culture as done in Tigard, Oreg., shows that the foregoing characteristics and distinctions come true to form and are established and transmitted through succeeding propagations.

BRIEF DESCRIPTION OF THE DRAWING

The drawing shows Heuchera 'Cherries Jubilee' blooming in Canby, Oreg.

DETAILED PLANT DESCRIPTION

The following is a detailed description of the new Heuchera hybrid based on observations of specimens in Canby, Oreg. The color descriptions are all based on *The Royal Horticultural Society Colour Chart* and the *American Rhododendron Society* publication: "A Contribution Toward Standardization of Color Names in Horticultre."

Foliage:

*Type.*—Evergreen.
*Shape.*—Cordate, 9-lobed.
*Length.*—6–7 cm (2.5–3 in).
*Width..*—7–8 cm (2.75–3.5 in).
*Petiole length.*—To 18 cm (7.25 in).
*Margins.*—Crenate-dentate, undulate.
*Apex.*—Obtuse.
*Base.*—Cordate-imbricate.
*Texture..*—Minutely hairy, glossy sheen.
*Leaf arrangement.*—Basal clump.
*Venation.*-Reticulate.

Flower:

*Petal count.*—5.
*Petal shape.*—Ovate.
*Flower type.*—Complete, Calyx tube urn-shaped.
*Flower shape.*—Campanulate.
*Ovary.*—Partly inferior.
*Carpels.*—2 cells.
*Stamens.*—5.
*Flower size.*—To 1 cm.
*Flower number.*—140 per panicle.
*Peduncle width.*—3 mm tapering to 1 mm.
*Blooming habit.*—Hoary panicles to 63 cm (25 in).
*Bloom period.*—In Oregon from late April to early June (6 weeks). Some rebloom has been observed.
*Fragrance.*—None.
*Lastingness on the plant.*—To 3 weeks (panicles).
*Lastingness off the plant.*—To 7 days (panicles).

Fruit:

*Fruit type.*—Dehiscent capsule.
*Fertility.*—Fertile.

Size:

*Height.*—25 cm (2-year-old plant grown in Tigard, Oreg.).
*Width.*—40 cm (2-year-old plant grown in Tigard, Oreg.).

Hardiness: Cold hardy to USDA Zone 4.

Disease: Susceptible to rot root when grown under wet conditions. Have not observed other diseases on plants grown in Canby, Oreg.

COLOR CHARACTERISTICS

Foliage:

*Mature leaves upper surface.*—Spring: R.H.S. 187A, Greyed Purple Group (Dark Red ARS) overlay of R.H.S 188B (Light Greenish Grey ARS).
*Lower surface.*—R.H.S. 58A, Red Purple Group (Moderate Purplish Red ARS).

Flowers:

*Upper petal surface.*—R.H.S. 52A Red Group (Vivid Red ARS).
*Lower petal surface.*—R.H.S. 52D Red Group (Deep Pink ARS).

Peduncle: R.H.S. Yellow Green Group 148A suffused with R.H.S. Red Purple Group 59A.
Fruit: R.H.S. Green Group 143B.

DESCRIPTION OF PARENT PLANTS

*Heuchera sanguinea* seedling is described for its intense red flower coloration. Heuchera 'Whirlwind' is described as having foliage that is remarkably fluted and bronze. It has pink and white flowers on sometimes-fasciated stalks. No other Heuchera plant in commerce known to me resembles Heuchera 'Cherries Jubilee'.

I claim:

1. A new and distint hybrid of Heuchera plant substantially as shown and described, characterized by distinct cherry-red flowers and chocolate-toned foliage.

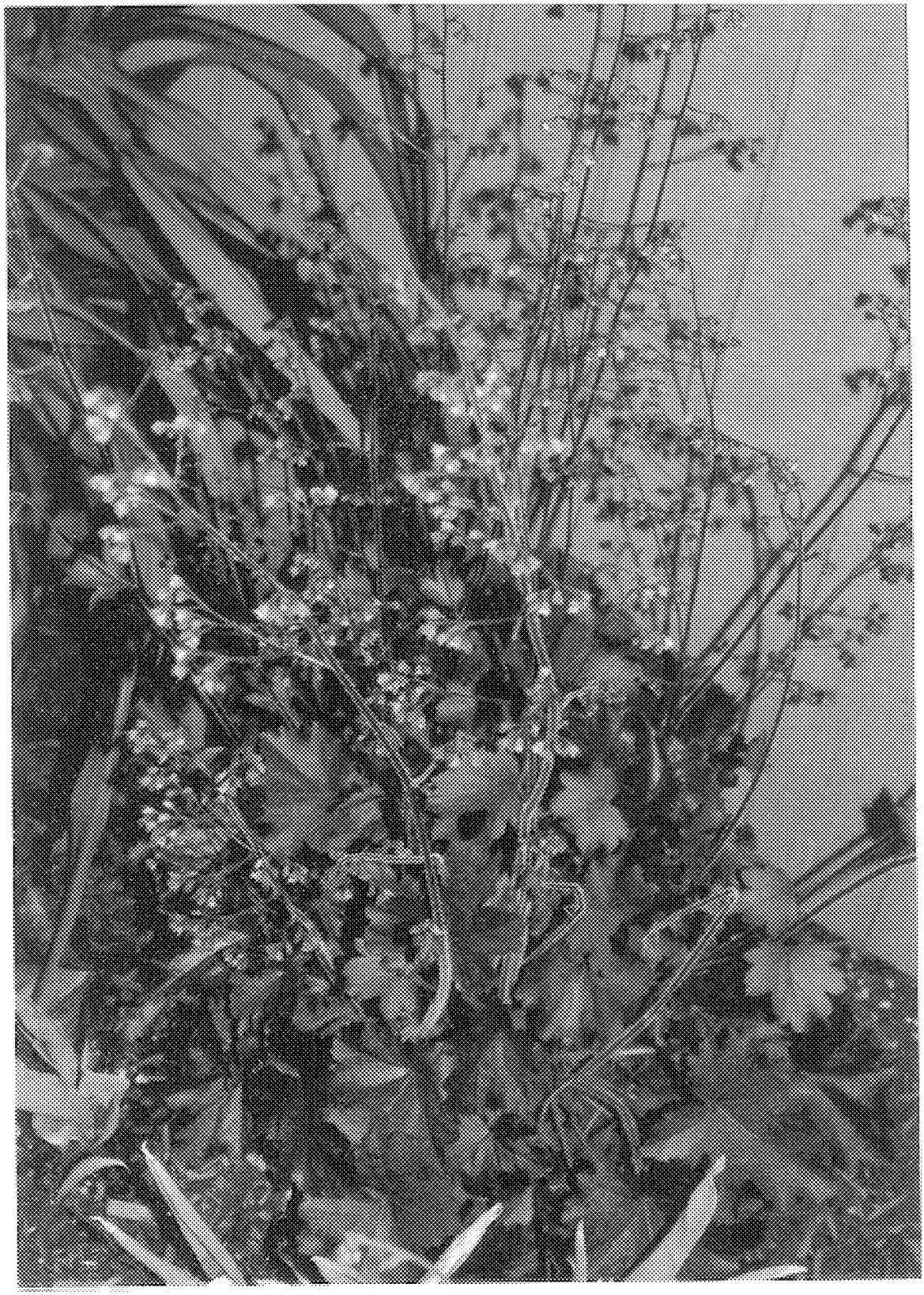

* * * * *